US012773466B2

(12) United States Patent
Joo et al.

(10) Patent No.: US 12,773,466 B2
(45) Date of Patent: Oct. 27, 2026

(54) STERILIZATION APPARATUS AND HOME APPLIANCE COMPRISING SAME

(71) Applicant: SAMSUNG ELECTRONICS CO., LTD., Suwon-si (KR)

(72) Inventors: Jongwook Joo, Suwon-si (KR); Youngchul Ko, Suwon-si (KR); Donghyo Kim, Suwon-si (KR); Myungju Shin, Suwon-si (KR); Hyunmin Kim, Yongin-si (KR); Jegu Mun, Seongnam-si (KR); Jingam Park, Seongnam-si (KR); Sunyoung Choi, Gwangju-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 462 days.

(21) Appl. No.: 18/545,121

(22) Filed: Dec. 19, 2023

(65) Prior Publication Data

US 2024/0115755 A1 Apr. 11, 2024

Related U.S. Application Data

(63) Continuation of application No. PCT/KR2022/011436, filed on Aug. 3, 2022.

(30) Foreign Application Priority Data

Aug. 20, 2021 (KR) ........................ 10-2021-0110268

(51) Int. Cl.
*A61L 9/20* (2006.01)

(52) U.S. Cl.
CPC ........... *A61L 9/20* (2013.01); *A61L 2209/134* (2013.01); *A61L 2209/14* (2013.01)

(58) Field of Classification Search
CPC ........................................................ A61L 9/20
See application file for complete search history.

(56) References Cited

U.S. PATENT DOCUMENTS 6,398,970 B1 6/2002 Justel et al.
6,783,578 B2 8/2004 Tillman, Jr.
(Continued)

FOREIGN PATENT DOCUMENTS

EP 1491218 A1 12/2004
JP 2001-170145 6/2001
(Continued)

OTHER PUBLICATIONS

Search Report and Written Opinion dated Nov. 23, 2023 issued in International Patent Application No. PCT/KR2022/011436.
(Continued)

*Primary Examiner* — Kevin Joyner
(74) *Attorney, Agent, or Firm* — Nixon & Vanderhye, P.C.

(57) ABSTRACT

A sterilizing apparatus and a home appliance comprising the same are provided. The sterilizing apparatus may include: a lamp body containing a gas configured to emit ultraviolet rays through electric discharge and having a cylindrical shape, a plurality of external electrodes disposed on an outer circumferential surface of the lamp body and extending in a longitudinal direction of the lamp body, and a cover including an inner wall and an outer wall, and provided in a radial direction of the lamp body to allow the inner wall to face the outer circumferential surface of the lamp body and outer surfaces of the plurality of external electrodes, wherein the lamp body includes a light-emitting region provided on the outer circumferential surface of the lamp body, the light-emitting region disposed between the plurality of external electrodes and configured to allow light emitted from the lamp body to be transmitted, wherein the cover is configured
(Continued)

to cover at least a portion of the light-emitting region to scatter the light emitted from the lamp body.

19 Claims, 12 Drawing Sheets

(56) References Cited

U.S. PATENT DOCUMENTS

| | | | |
|---|---|---|---|
| 9,974,881 | B2 | 5/2018 | Kim et al. |
| 10,160,667 | B2 | 12/2018 | Vecziedins et al. |
| 11,028,223 | B2 | 6/2021 | Niemiec et al. |
| 11,621,157 | B2 | 4/2023 | Shin et al. |
| 2007/0090740 | A1 | 4/2007 | Hiraoka et al. |
| 2014/0140893 | A1 | 5/2014 | Kohler |
| 2018/0021469 | A1 | 1/2018 | Kim et al. |
| 2018/0021470 | A1 | 1/2018 | Kim et al. |
| 2019/0389745 | A1 | 12/2019 | Schwarz-Kiene et al. |

FOREIGN PATENT DOCUMENTS

| | | |
|---|---|---|
| JP | 2001-238939 | 9/2001 |
| JP | 2002-289146 | 10/2002 |
| JP | 2005-093108 | 4/2005 |
| JP | 2007-533441 | 11/2007 |
| JP | 4470833 | 6/2010 |
| JP | 6234424 | 11/2017 |
| JP | 2020-512191 | 4/2020 |
| KR | 10-2005-0019692 | 3/2005 |
| KR | 10-2007-0002781 | 1/2007 |
| KR | 10-2007-0017898 | 2/2007 |
| KR | 10-0680310 | 2/2007 |
| KR | 10-0746096 | 8/2007 |
| KR | 20-0442437 | 11/2008 |
| KR | 10-2010-0075323 | 7/2010 |
| KR | 10-2018-0010876 | 1/2018 |
| KR | 10-2019-0020442 | 3/2019 |
| KR | 10-2186476 | 12/2020 |
| KR | 10-2198329 | 1/2021 |
| KR | 10-2242187 | 4/2021 |
| KR | 10-2022-0126168 | 9/2022 |
| WO | 2005-102401 | 11/2005 |
| WO | 2014-116066 | 7/2014 |
| WO | 2018-158313 | 9/2018 |

OTHER PUBLICATIONS

Office Action dated May 14, 2026 in Korean Application No. 10-2021-0110268 with English translation.

STERILIZATION APPARATUS AND HOME APPLIANCE COMPRISING SAME

CROSS-REFERENCE TO RELATED APPLICATIONS

This application is a continuation of International Application No. PCT/KR2022/011436 designating the United States, filed on Aug. 3, 2022, in the Korean Intellectual Property Receiving Office and claiming priority to Korean Patent Application No. 10-2021-0110268, filed on Aug. 20, 2021, in the Korean Intellectual Property Office, the disclosures of each of which are incorporated by reference herein in their entireties.

BACKGROUND

Field

The disclosure relates to a sterilizing apparatus and a home appliance including the same, and for example, to a sterilizing apparatus using ultraviolet rays and a home appliance including the same.

Description of Related Art

In general, conventional fluorescent lamps are of two types: those with internal electrodes inside a glass tube, such as hot cathode fluorescent lamps (HCFLs) and cold cathode fluorescent lamps (CCFLs), and those with external electrodes outside the glass tube, such as external electrode fluorescent lamps (EEFLs).

EEFLs, for example, produce light by inducing an electrical discharge using the glass tube itself as a dielectric, and may be operated at low voltages, providing advantages over CCFLs in terms of lifetime and power consumption.

Among EEFLs, there are also lamps in which a pair of band-shaped external electrodes are placed facing each other along a direction of extension of a glass tube on an outer surface thereof in order to induce electric discharge by the glass tube itself acting as a dielectric, which are also referred to as counter-electrode capacitive discharge lamps. Hereinafter, EEFLs including the pair of band-shaped electrodes on the outer surface of the glass tube along the direction of extension of the glass tube will be referred to as opposed external electrode fluorescent lamps.

The opposed external electrode fluorescent lamps include a glass tube filled with a rare gas (e.g., inert gas), such as xenon gas, and an inner surface thereof is coated with a fluorescent material, and an outer surface thereof is attached with a pair of band-shaped external electrodes arranged to face each other. The pair of band-shaped electrodes may be directly connected to a metal holder that clamps the lamp at opposite ends to apply a voltage, or may be connected to cap electrodes placed at the opposite ends of the lamp and the cap electrodes are connected to the holder to apply a voltage.

When the metal holder is connected to an inverter and an external power source and a high-frequency alternating voltage is applied to the pair of band-shaped external electrodes, an electric discharge occurs through xenon gas, and ultraviolet rays are emitted through an excimer reaction.

However, light emitted from the lamp does not penetrate the external electrodes disposed on the outer surface of the lamp, resulting in a shaded area, and when sterilizing a cylindrical object, the sterilizing function may be reduced due to the shaded area.

SUMMARY

Embodiments of the disclosure may provide a sterilizing apparatus capable of uniformly irradiating ultraviolet rays to a shaded area created by external electrodes, and a home appliance including the same.

According to an example embodiment of the disclosure, a sterilizing apparatus includes: a lamp body containing a gas configured to emit ultraviolet rays through electric discharge and having a cylindrical shape, a plurality of external electrodes disposed on an outer circumferential surface of the lamp body and extending in a longitudinal direction of the lamp body, and a cover including an inner wall and an outer wall, and provided in a radial direction of the lamp body to allow the inner wall to face the outer circumferential surface of the lamp body and outer surfaces of the plurality of external electrodes, wherein the lamp body includes a light-emitting region on the outer circumferential surface of the lamp body, the light-emitting region disposed between the plurality of external electrodes and configured to allow light emitted from the lamp body to be transmitted, wherein the cover is configured to cover at least a portion of the light-emitting region and to scatter the light emitted from the lamp body.

The inner wall of the cover may be arranged to be spaced apart in the radial direction of the lamp body from the outer circumferential surface of the lamp body and the outer surfaces of the plurality of external electrodes.

The cover may have a cylindrical shape surrounding the lamp body and the plurality of external electrodes.

A cross-section of the cover may be concentric with a cross-section of the lamp body.

The lamp body may include a non-light-emitting region on the outer circumferential surface of the lamp body, the non-light-emitting region may be configured such that light emitted from the lamp body is not allowed to be transmitted by the plurality of external electrodes, and the cover may be configured such that at least a portion of the light transmitted through the cover is scattered in a direction corresponding to a radial direction of the non-light-emitting region.

The cover may have a thickness of 0.2 mm or more and 1.5 mm or less.

When an average value of a radius of the outer wall and a radius of the inner wall of the cover is r2 and a radius of the lamp body is r1, a ratio of r2 and r1 may be 1.5 or more.

The sterilizing apparatus may further include a fixing piece configured to fix the cover and the lamp body.

The fixing piece may be provided at opposites ends of the cover to fix the lamp body and the opposite ends of the cover.

The fixing piece may include a first fixing portion provided on the outer circumferential surface of the lamp body, a second fixing portion provided on the cover, and at least one connection portion connecting the first fixing portion and the second fixing portion, and the connection portion may include at least one hole configured to allow the exterior of the cover to communicate with the interior of the cover.

The fixing piece may have a cylindrical shape including a hollow and an inner surface forming the hollow, wherein the inner surface is connected to the lamp body.

The cover and the lamp body may be fixed by the fixing portion so that the inner wall of the cover is disposed to be spaced apart from outer surfaces of the plurality of external electrodes in the radial direction of the lamp body.

The sterilizing apparatus may further include a plurality of cap electrodes fixed to opposite ends of the lamp body configured to apply power to the plurality of external electrodes, each of the plurality of external electrodes may be connected to only one of the plurality of cap electrodes.

The plurality of cap electrodes may have a cylindrical shape including a hollow.

The cover may comprise a fluororesin material.

According to an example embodiment of the disclosure, a home appliance includes: an inlet configured to draw in air, a blowing fan, a filter having a cylindrical shape including a hollow and configured to purify the air entering the inlet, an outlet configured to discharge air passing through the filter, a sterilizing apparatus comprising a lamp disposed inside the filter, and a housing including the inlet and the outlet and including the blowing fan, the filter and the sterilizing apparatus, wherein the sterilizing apparatus includes: a lamp body containing a gas configured to emit ultraviolet rays through electric discharge and having a cylindrical shape, a pair of external electrodes extending in a longitudinal direction of the lamp body and disposed on an outer circumferential surface of the lamp body to face each other with respect to a central axis of the lamp body, and a cover including an inner wall and an outer wall provided in a radial direction of the lamp body to allow the inner wall to face the outer circumferential surface of the lamp body and outer surfaces of the pair of external electrodes, wherein the lamp body includes a light-emitting region on the outer circumferential surface of the lamp body, the light-emitting region disposed between the pair of external electrodes configured to allow light emitted from the lamp body to be transmitted, wherein the cover is configured to cover at least a portion of the light-emitting region and to scatter the light emitted from the lamp body.

The sterilizing apparatus may further comprise a support configured to be coupled to the filter.

The support may be formed radially.

Cross-sections of the cover and the lamp body may be arranged to be concentric with a cross-section of the filter, and based on an average value of a radius of the outer wall and the inner wall of the cover being r2 and a radius of the lamp body being r1, a ratio of r2 and r1 may be 2 or less.

According to an example embodiment of the disclosure, a sterilizing apparatus includes: a lamp body containing a gas configured to emit ultraviolet rays through electric discharge and having a cylindrical shape, a pair of external electrodes extending in a longitudinal direction of the lamp body and disposed on an outer circumferential surface of the lamp body to face each other with respect to an central axis of the lamp body, and a cover including an inner wall and an outer wall arranged in the longitudinal direction of the lamp body and provided in a radial direction of the lamp body to allow the inner wall to face the outer circumferential surface of the lamp body and outer surfaces of the pair of external electrodes, wherein the lamp body includes: a light-emitting region and a non-light-emitting region on the outer circumferential surface of the lamp body, the light-emitting region disposed between the pair of external electrodes and configured to allow light emitted from the lamp body to be transmitted, the non-light-emitting region configured such that light emitted from the lamp body is not allowed to be transmitted by the plurality of external electrodes, wherein the cover is configured to cover at least a portion of the light-emitting region to scatter the light emitted from the light-emitting region, and the cover may be configured such that at least a portion of the light transmitted through the cover is scattered to an external region of the non-light-emitting region in the radial direction of the lamp body.

According to various example embodiments of the present disclosure, the sterilizing apparatus includes the cover for covering the lamp body and the external electrodes, thereby uniformly irradiating ultraviolet rays to a shaded area generated by the external electrodes.

BRIEF DESCRIPTION OF THE DRAWINGS

The above and other aspects, features and advantages of certain embodiments of the present disclosure will be more apparent from the following detailed description, taken in conjunction with the accompanying drawings, in which.

DETAILED DESCRIPTION

Figure 1:
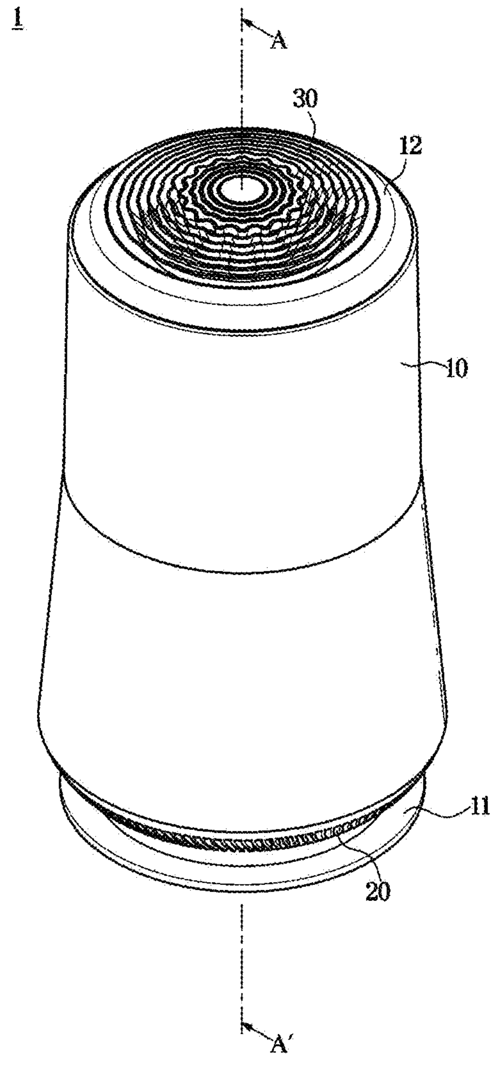
FIG. 1 is a perspective view illustrating an air purifier including a sterilizing apparatus according to various embodiments.

The various example embodiments described in the disclosure and configurations shown in the drawings are merely examples of the embodiments of the disclosure and may be modified in various different ways at the time of filing of the present application.

In addition, the same reference numerals or signs shown in the drawings of the disclosure indicate elements or components performing substantially the same function.

Also, the terms used herein are used to describe the embodiments and are not intended to limit and/or restrict the disclosure. The singular forms “a,” “an” and “the” are intended to include the plural forms as well, unless the context clearly indicates otherwise. In this disclosure, the terms “including”, “having”, and the like are used to specify features, figures, steps, operations, elements, components, or combinations thereof, but do not preclude the presence or addition of one or more of the features, figures, steps, operations, elements, components, or combinations thereof.

It will be understood that, although the terms first, second, primary, secondary, etc., may be used herein to describe various elements, but elements are not limited by these terms. These terms are simply used to distinguish one element from another element. For example, without departing from the scope of the disclosure, a first element may be termed as a second element, and a second element may be termed as a first element. The term of "and/or" includes a plurality of combinations of relevant items or any one item among a plurality of relevant items.

Hereinafter, various example embodiments according to the disclosure will be described in greater detail with reference to the accompanying drawings.

Furthermore, for ease of description, an air purifier, which is a type of home appliance, is described herein as an example, but a configuration including a sterilizing apparatus according to an embodiment of the disclosure is not limited thereto, and may, for example, and without limitation, be employed to any home appliance that requires sterilization using light. For example, the disclosure may also be applied to home appliances, such as vacuum cleaners, air conditioners, dehumidifiers, and the like. In addition, any home appliance including a cylindrical filter may be used. However, an object to be sterilized is not limited to the cylindrical filter, and may not be a filter or may not have a cylindrical shape.

Figure 2:
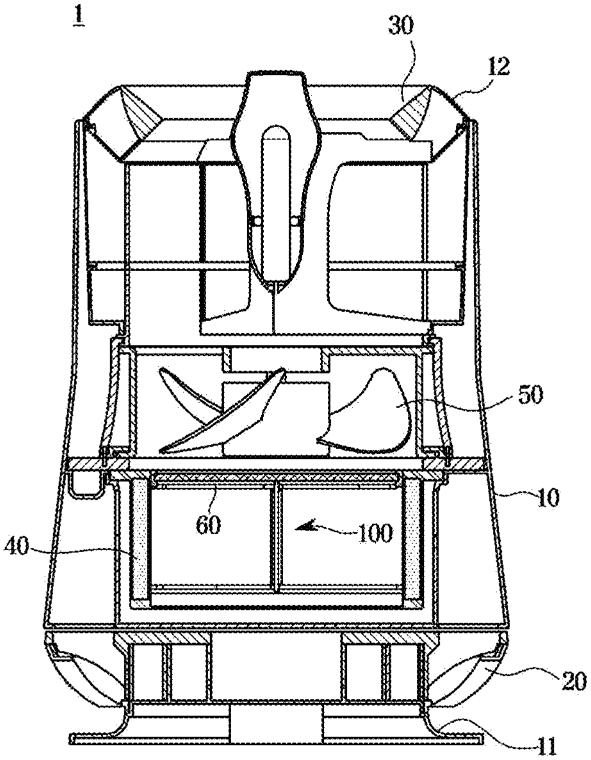
FIG. 2 is a cross-sectional view taken along line A-A' of the air purifier of FIG. 1 according to various embodiments.

FIG. 1 is a perspective view illustrating an example air purifier including a sterilizing device according to various embodiments. FIG. 2 is a cross-sectional view taken along line A-A' of the air purifier of FIG. 1 according to various embodiments.

Referring to FIGS. 1 and 2, an air purifier 1 may include an inlet provided in a housing 10 of the air purifier 1 to allow air to be drawn in, and an outlet 30 provided in the housing 10 of the air purifier 1 to allow the air drawn in through the inlet to be discharged. The inlet 20 and the outlet 30 may be formed on different surfaces or on the same surface. The inlet 20 may be formed on a lower surface 11 of the housing 10 of the air purifier 1. The outlet 30 may be formed on an upper surface 12 of the housing 10 of the air purifier 1. However, the arrangement of the inlet 20 and the outlet 30 is not limited thereto, and may be formed on a front surface, a rear surface, or a side surface of the air purifier 1.

The air purifier 1 may include a filter 40 and a blowing fan 50 within the housing 10. The blowing fan 50 may draw external air into the inside of the air purifier 1 through the inlet 20, filter the drawn-in external air by passing it through the filter 40, and then discharge the filtered external air to the outside of the air purifier 1 through the outlet 30. The filter 40 may purify the air drawn in from the inlet 20 and may be detachably mounted on the air purifier 1.

The filter 40 may be formed in a cylindrical shape. In other words, the filter 40 may have a hollow cylindrical shape and may be provided to purify the air flowing into the inlet 20. However, the disclosure is not limited thereto, and the filter 40 may be formed in various shapes, such as a planar shape or a hollow rectangular parallelepiped shape, and may be provided in a plurality. Hereinafter, for ease of description, the filter 40 will be described as having the hollow cylindrical shape.

The air purifier 1 may include a sterilizing apparatus 100, and the sterilizing apparatus 100 may be disposed within the housing 10. For example, the sterilizing apparatus 100 may be provided inside the filter 40 having the cylindrical shape. The sterilizing apparatus 100 may be formed in the cylindrical shape and may be provided within the filter 40 in a direction parallel to the filter 40. The sterilizing apparatus 100 may be configured to be coupled to the filter 40. For example, the sterilizing apparatus 100 may be coupled to the filter 40 by a supporter (e.g., including a support) 60. The sterilizing apparatus 100 may be detachably coupled to the filter 40. However, an arrangement and shape of the sterilizing apparatus 100 and any manner of coupling the sterilizing apparatus 100 to the filter 40 are not limited thereto, and various arrangements, shapes, and any manner thereof may be used depending on the type of the filter 40 or other objects to be sterilized (not shown). Furthermore, the sterilizing apparatus 100 may be coupled to the filter 40 without the supporter 60, or may not be coupled to the filter 40.

The air purifier 1 may include the supporter 60, and the supporter 60 may be disposed within the housing 10. The supporter 60 may allow the sterilizing apparatus 100 to be coupled to the filter 40. The supporter 60 may be formed to connect at least one of opposite ends of the sterilizing apparatus 100 and the filter 40, or may be formed to connect the opposite ends of the sterilizing apparatus 100 to the filter 40. However, the disclosure is not limited thereto, and the supporter 60 may be formed to support a different portion of the sterilization device 100 instead of the opposite ends of the sterilization device 100, so that the sterilizing apparatus 100 may be coupled to the filter 40.

As such, the air purifier 1, as shown in FIG. 1, may include the inlet 20 in which air is drawn in, the blowing fan 50, the filter 40 having the hollow cylindrical shape and provided to purify the air flowing into the inlet 20, the outlet 30 to which the air passing through the filter 40 is discharged, the sterilizing apparatus 100 provided within the filter 40, the supporter configured to couple the sterilizing apparatus 100 to the filter 40, and the housing 10 in which the inlet 20 and the outlet 30 are provided and receiving the blowing fan 50, the filter 40, and the sterilizing apparatus 100. However, the disclosure is not limited thereto, and a configuration of the air purifier 1 including the sterilizing apparatus 100 may have various features.

Figure 3:
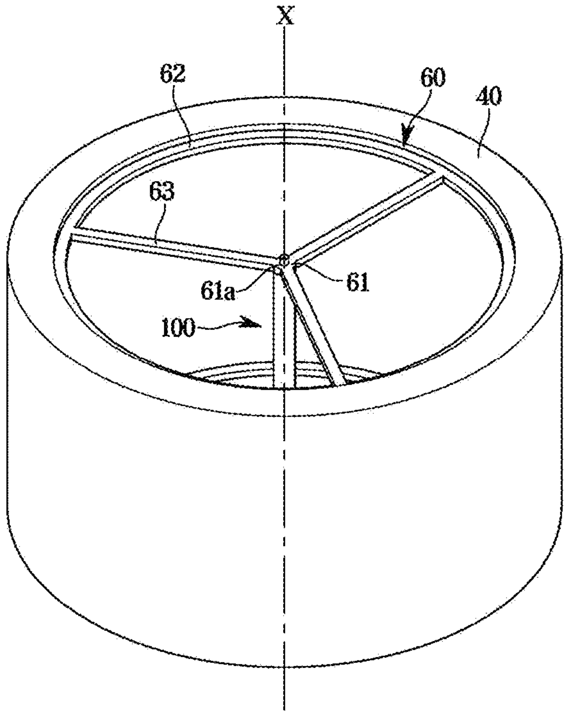
FIG. 3 is a perspective view illustrating a filter and the sterilizing apparatus of the air purifier shown in FIG. 2 according to various embodiments.

FIG. 3 is a perspective view illustrating the filter and sterilizing apparatus of the air purifier shown in FIG. 2 according to various embodiments.

Referring to FIG. 3, the filter 40 of the air purifier 1 may have the hollow cylindrical shape. The sterilizing apparatus 100 may be provided within the filter 40. The sterilizing apparatus 100 may be provided within the filter 40 in a direction parallel to the filter 40 (X direction). Accordingly, light emitted from the sterilizing apparatus 100 may be uniformly irradiated to the inside of the filter 40 in an axial direction of the filter 40. As described above, the sterilizing apparatus 100 may be configured to be coupled to the filter 40 by the supporter 60. The configuration and features of the sterilizing apparatus 100 will be described later.

The supporter (e.g., support) 60 may be formed to connect at least one of the opposite ends of the sterilizing apparatus 100 to the filter 40. The supporter 60 may be formed such that the opposite ends of the sterilizing apparatus 100 are connected to the filter 40. However, the disclosure is not limited thereto, and the supporter 60 may be formed to support a different portion of the sterilizing apparatus 100 instead of the opposite ends of the sterilizing apparatus 100, so that the sterilizing apparatus 100 may be coupled to the filter 40.

The supporter 60 may be arranged such that the cross-section of the filter 40 is concentric with the cross-section of the sterilizing apparatus 100. Further, the supporter 60 may be arranged such that the cross-section of the filter 40 is concentric with the cross-sections of a lamp body 110 and the cover 130, which will be described in greater detail below. In other words, as shown in FIG. 3, the filter 40 and the sterilizing apparatus 100 may be arranged with the X direction as the central axis thereof. In this case, the sterilizing apparatus 100 may be positioned at the center of the filter 40 by the supporter 60, and thus the light emitted from the sterilizing apparatus 100 may be uniformly irradiated to the filter 40.

In the case where the supporter 60 is arranged such that the cross-section of the filter 40 is concentric with the cross-sections of the lamp body 110 and the cover 130, the following conditions may be satisfied with respect to the specifications of the cover 130 and the filter 40. A ratio of an average value r2 of the radius of an outer wall 131 and the radius of an inner wall 132 of the cover 130 to a distance d from the midpoint M of the outer wall 131 and the inner wall 132 of the cover 130 to the filter 40 may be satisfied to be 2 or less. However, the disclosure is not limited thereto, and the cover 130 and filter 40 may have different specifications in terms of shape and arrangement.

The supporter 60 may include a first supporter 61 provided in the sterilizing apparatus 100, a second supporter 62 provided in the filter 40, and a third supporter 63 connecting the first supporter 61 and the second supporter 62. The first supporter 61 may be provided on the at least one of opposite ends of the sterilizing apparatus 100, and may have a coupling groove 61*a* to couple the supporter 60 to the sterilizing apparatus 100. The second supporter 62 may be provided along an inner circumferential surface of the filter 40. However, the features of the first supporter and the second supporter are not limited thereto.

The supporter 60 may be formed radially. That is, the supporter 60 may be formed such that a plurality of third supporters 63 connect the first supporter 61 and the second supporter 62 and are in communication with the inside and outside of the filter 40. The third supporter 63 may be formed in a plurality, such as three or more and may be formed in a straight line. In addition, the third supporter 63 may have a width of 2 mm or more and 10 mm or less. When the supporter 60 is formed in a radial shape, the sterilizing apparatus 100 may be stably attached to the filter 40 while the heat generated by the sterilizing apparatus 100 may be easily dissipated to the outside. In addition, since the supporter 60 is formed radially, the light emitted from the sterilizing apparatus 100 may sterilize any configuration of the air purifier 1 located outside of the filter 40, such as the blowing fan 50. However, the shape and number of the third supporters 63 and the shape of the supporter 60 are not limited thereto. The third supporter 63 may be formed in a non-straight line.

The supporter 60 may be configured to detachably couple the sterilizing apparatus 100 to the filter 40. In this case, at least one of the sterilizing apparatus 100 or the filter 40 may be easily replaceable, detachable, or attachable, but is not limited thereto.

Furthermore, the supporter 60 may comprise a fluororesin material, which may be more resistant to deterioration by ultraviolet rays. However, the material of the supporter 60 is not limited thereto and may comprise a variety of materials.

As such, the supporter 60 may be configured to couple the sterilizing apparatus 100 to the filter 40, include the first supporter 61, the second supporter 62, and the third supporter 63, and be formed radially. In addition, the supporter 60 may be configured to detachably couple the sterilizing apparatus 100 to the filter 40 and may be made of a fluororesin material. However, the features of the supporter 60 are not limited thereto, and the supporter 60 may have different shapes and materials. In the following, the sterilizing apparatus 100 may be coupled to the filter 40 by the supporter 60 as an example, but the sterilizing apparatus 100 may be supported in various ways.

Figure 4:
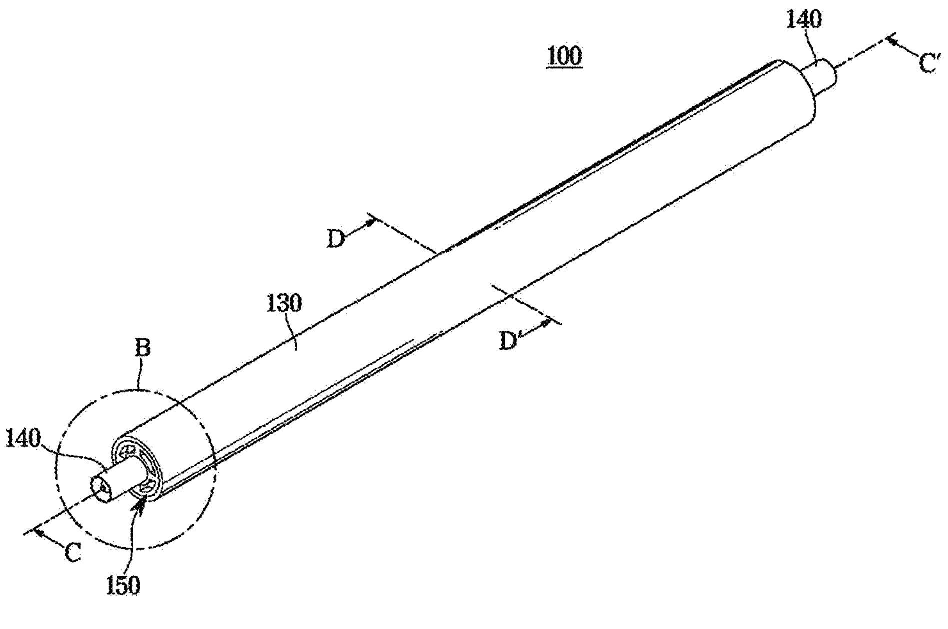
FIG. 4 is a perspective view illustrating the sterilization device according to various embodiments.
Figure 5:
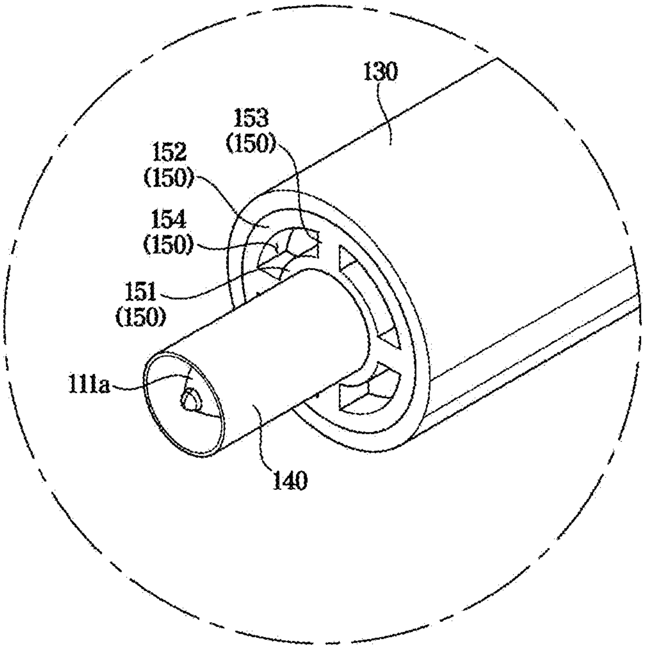
FIG. 5 is a partial perspective view illustrating an enlarged view of B in FIG. 4 according to various embodiments.
Figure 6:
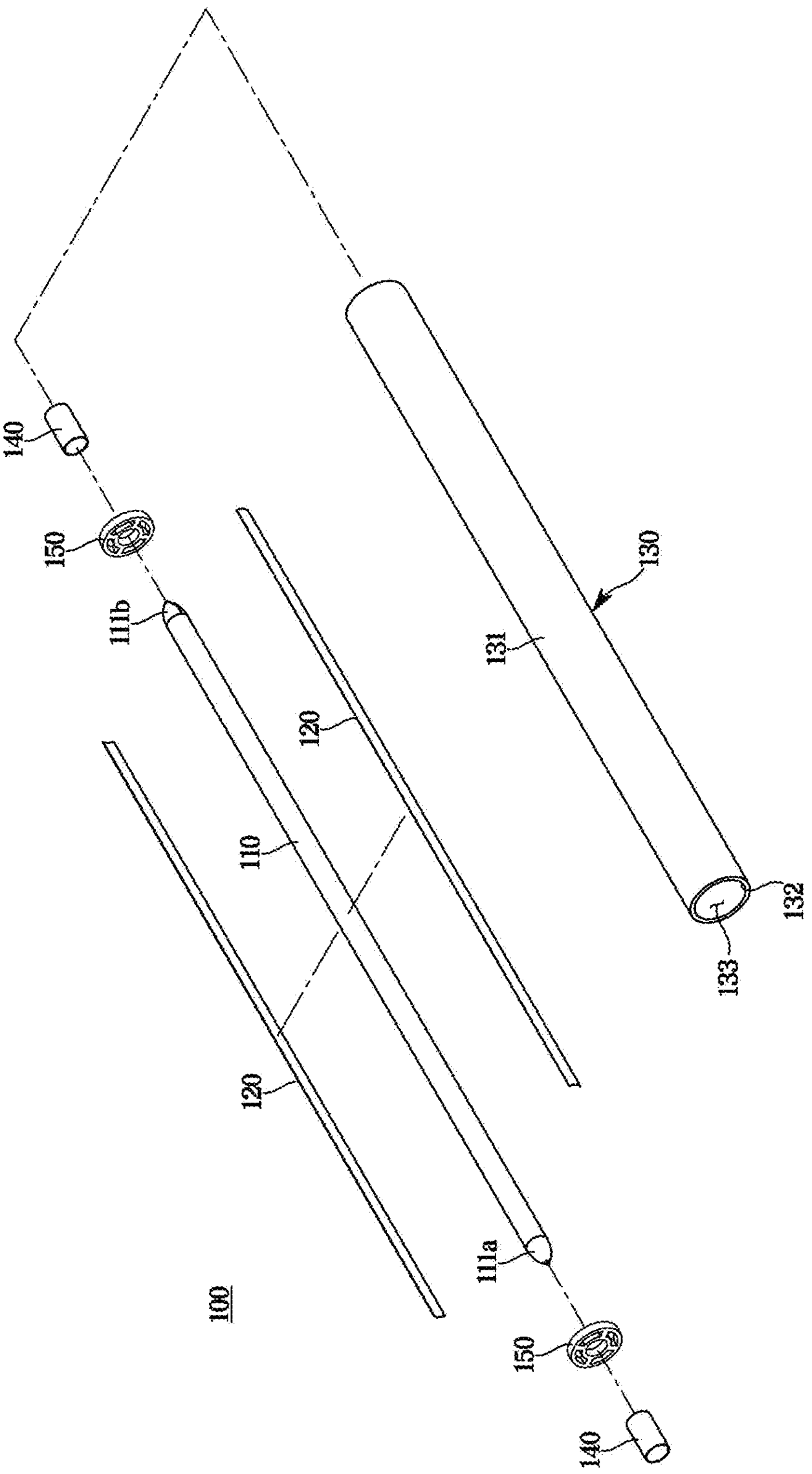
FIG. 6 is an exploded perspective view of the sterilizing apparatus of FIG. 4 according to various embodiments.
Figure 7:
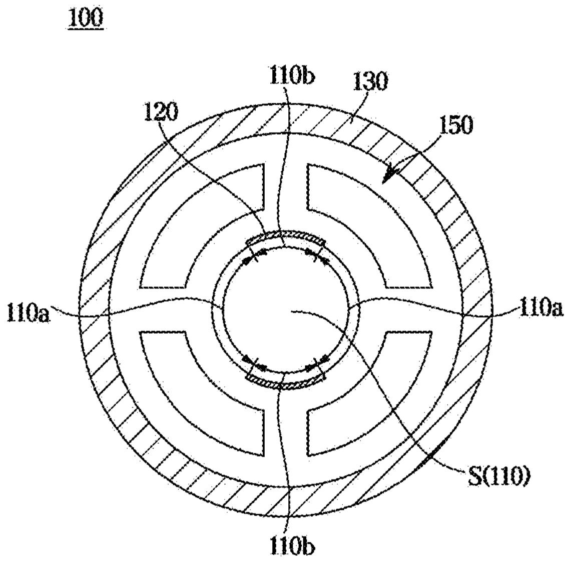
FIG. 7 is a cross-sectional view taken along line D-D' of the sterilizing apparatus of FIG. 4 according to various embodiments.
Figure 8:
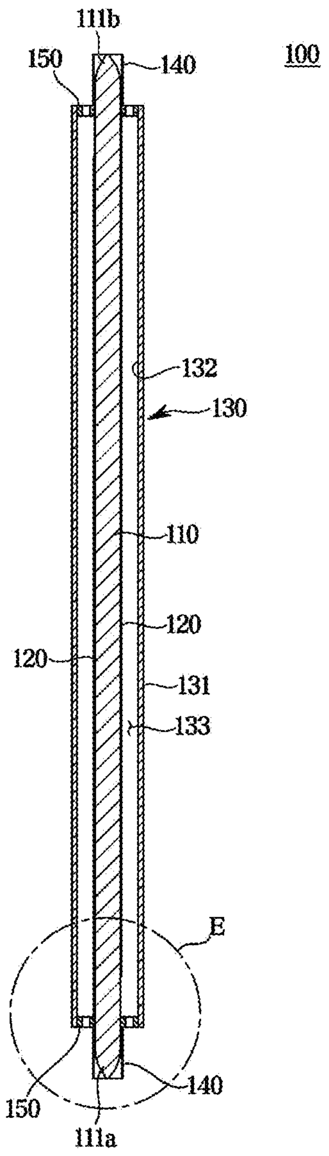
FIG. 8 is a longitudinal cross-sectional view taken along line C-C' of the sterilizing apparatus of FIG. 4 according to various embodiments.
Figure 9:
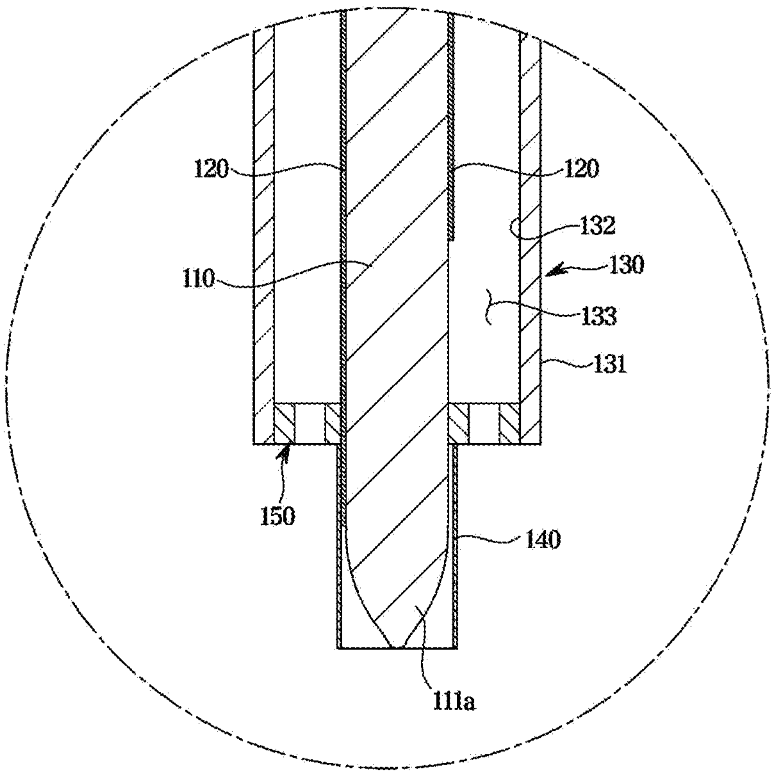
FIG. 9 is a cross-sectional view illustrating an enlarged view of E in FIG. 8 according to various embodiments.

FIG. 4 is a perspective view illustrating an example sterilizing apparatus according to various embodiments. FIG. 5 is an enlarged perspective view of B in FIG. 4 according to various embodiments. FIG. 6 is an exploded perspective view of the sterilizing apparatus of FIG. 4 according to various embodiments. FIG. 7 is a cross-sectional view taken along line D-D' of the sterilizing apparatus of FIG. 4 according to various embodiments. FIG. 8 is a longitudinal cross-sectional view taken along line C-C' of the sterilizing apparatus of FIG. 4 according to various embodiments. FIG. 9 is a partial cross-sectional view illustrating an enlarged view of E in FIG. 8 according to various embodiments.

Referring to FIGS. 4, 5, 6, 7, 8 and 9 (which may be referred to herein as FIGS. 4 to 9), the sterilizing apparatus 100 according to an embodiment of the present disclosure may include the lamp body 110 from which light is emitted, a plurality of external electrodes 120 to which power is applied, and a cover 130 provided on the lamp body 110 in a radial direction.

The lamp body 110 may contain a gas (not shown) that emits ultraviolet rays through an electrical discharge and may have a cylindrical shape.

The material of the lamp body 110 may comprise quartz tube or borosilicate glass for efficient transmission of ultraviolet rays. The lamp body 110 may be provided in the cylindrical shape and may extend in one direction (e.g., front-to-back direction). The lamp body 110 may be provided in a tubular shape with opposite ends 111*a* and 111*b* closed. A plurality of cap electrodes 140 may be provided and attached to the opposite ends 111*a* and 111*b* of the lamp body 110, respectively.

The lamp body 110 may include an electric discharge space S that is hollowly provided therein. The inside of the lamp body 110 may contain a gas that emits ultraviolet rays through electric discharge. For example, and without limitation, noble gases, etc. may be used as a gas that emits ultraviolet rays through electric discharge. When a voltage is applied to the gas, such as a noble gas in its ground state, an excited dimer molecule (hereinafter referred to as an excimer) is created. Because the excimer is in an unstable state, it immediately returns to the ground state, and emits ultraviolet rays in this process. An encapsulating gas inside the lamp body 110 may include xenon (Xe) or xenon mixed gas (e.g., Xe, Ar, Ne, etc.). An inner wall of the lamp body 110 may be coated with a phosphor (not shown) capable of converting the emission wavelength band 172 nm of xenon to the sterilizing wavelength range of 250 to 260 nm. However, the gas accommodated within the lamp body 110 is not limited to a noble gas, such as xenon and mixed gases of noble gases, and various types of gas may be provided as long as it is capable of emitting light in the ultraviolet region through electric discharge. The lamp body 110 may accommodate a phosphor therein depending on the wavelength of the ultraviolet rays to be emitted.

To implement an external electrode fluorescent light (EEFL) type lamp, an external electrodes 120 are formed on a surface of the lamp body 110. The external electrodes 120 may be disposed on an outer surface of the lamp body 110 and may be provided to extend along a direction in which the lamp body 110 extends (e.g., front-to-back direction). In other words, the external electrodes 120 may be disposed on an outer circumferential surface of the lamp body 110 and may be provided to extend in a longitudinal direction of the lamp body 110.

The external electrode 120 may include the plurality of external electrodes 120. For example, the plurality of external electrodes 120 may be provided as a pair of external electrodes 120 and may be disposed on the outer circumferential surface of the lamp body 110 such that the pair of external electrodes 120 face each other relative to a central axis of the lamp body 110.

Each of the external electrodes 120 may be provided in the form of a tape on the surface of the lamp body 110. The material of the external electrode 120 is not particularly limited as long as it has conductivity. For example, the external electrode 120 may comprise gold, silver, nickel, carbon, gold palladium, silver palladium, platinum, aluminum, or alloys thereof.

The external electrode 120 may be applied with power directly from an external power source (not shown), but may also be applied with power through the cap electrodes 140 attached to the opposite ends 111*a* and 111*b* of the lamp body 110. For example, the plurality of cap electrodes 140 may be provided and attached to each ends 111*a* and 111*b* of the lamp body 110, and may be connected to an external power source and connected to apply power to the plurality of external electrodes 120. Each of the plurality of external electrodes 120 may be connected correspondingly to only one of the plurality of cap electrodes 140. That is, one of the pair of external electrodes 120 may be connected to only one of the pair of cap electrodes 140 to be energized, and the other one of the pair of external electrodes 120 may be connected to only the other one of the pair of cap electrodes 140 to be energized. However, the manner in which the external electrodes 120 are energized is not limited thereto.

The cap electrodes 140 may be provided in pairs and attached to the opposite ends 111*a* and 111*b* of the one lamp body 110, respectively. The respective cap electrode 140 may be provided in a cylindrical shape including a hollow corresponding to the outer surface of the lamp body 110. The material of the cap electrode is not particularly limited as long as it has conductivity, and may comprise, for example, gold, silver, nickel, carbon, gold palladium, silver palladium, platinum, aluminum, or alloys thereof. However, the disclosure is not limited thereto, and the cap electrode 140 may have different characteristics, such as arrangement, shape, and material.

The lamp body 110 may include a light-emitting region 110*a* and a non-light-emitting region 110*b*. With the external electrode 120 disposed on the outer surface of the lamp body 110, the light-emitting region 110*a* through which light emitted from the lamp body 110 is allowed to be transmitted and the non-emitting region 110*b* through which light emitted from the lamp body 110 is not allowed to be transmitted may be formed on the outer circumferential surface of the lamp body 110. For example, the light-emitting region 110*a* may be disposed between the plurality of external electrodes 120 provided on the outer circumferential surface of the lamp body 110, so that the light emitted from the lamp body 110 may be transmitted. Light emitted from the lamp body 110 may not be transmitted through the non-light-emitting region 110*b* due to the plurality of external electrodes 120 provided on the outer circumferential surface of the lamp body 110. Because the external electrodes 120 are arranged as a pair on the outer circumferential surface of the lamp body 110, the non-light-emitting region 110*b* may also be formed as a pair on the outer circumferential surface of the lamp body 110.

According to a conventional sterilizing apparatus including the lamp body 110 and the external electrode 120, a shaded area (not shown) may create where direct light emitted from the lamp body 110 does not reach the cylindrical filter 40 due to the non-light-emitting region 110*b*. As a result, the conventional sterilizing apparatus suffers from the sterilizing function being reduced by the shaded area.

The sterilizing apparatus 100 according to an embodiment of the present disclosure may include the cover 130 for covering at least a portion of the light-emitting region 110*a*. Accordingly, the at least a portion of the light emitted from the light-emitting region 110*a* may be scattered while transmitting through the cover 130. For example, at least a portion of the scattered light may be scattered in a radial direction of the non-light-emitting region 110*b* and reach the filter 40, thereby preventing and/or reducing a shadow region from occurring in the filter 40.

The cover 130 may include the inner wall 132 and the outer wall 131. The cover 130 may be formed in a hollow cylindrical shape as shown in FIG. 4. In this case, the inner wall 132 may form a receiving space 133 that accommodates the lamp body 110 and the external electrodes 120. For example, the cover 130 may be provided in the cylindrical shape surrounding the lamp body 110 and the external electrodes 120. In addition, the cross-section of the cover 130 may be provided to be concentric with the cross-section of the lamp body 110. In other words, as shown in FIG. 4, the cover 130 and the lamp body 110 may be formed in the cylindrical shape with a line extending from the line C-C' as a central axis. However, the disclosure is not limited thereto, and the cover 130 may be formed in different shapes and may be provided in a plurality.

The cover 130 may be provided in a radial direction of the lamp body 110, and thus the inner wall 132 of the cover 130 may face the outer circumferential surface of the lamp body 110. The inner wall 132 of the cover 130 may face an outer surface of the external electrode 120. However, even in this case, the cover 130 is required to be provided to cover at least a portion of the light-emitting region 110*a* in order to scatter the light emitted from the lamp body 110.

The inner wall 132 of the cover 130 may be arranged to be spaced apart from the outer circumferential surface of the lamp body 110 in the radial direction of the lamp body 110. In the case where the inner wall 132 of the cover 130 also faces the outer surface of the external electrode 120, the inner wall 132 of the cover 130 may be arranged to be spaced apart from the outer surface of the external electrode 120 in the radial direction of the lamp body 110. Such an arrangement may cause heat generated from the lamp body 110 and the external electrode 120 to be easily radiated to the outside of the sterilizing apparatus 100. However, the disclosure is not limited thereto, and the inner wall 132 of the cover 130 may be arranged to be in close contact with the outer surface of the lamp body 110 or the outer surface of the external electrode 120.

The cover 130 may comprise a translucent material so that the light emitted from the lamp body 110 may be transmitted and scattered. In addition, the cover 130 may comprise a fluororesin-based material to prevent and/or reduce the material from being deteriorated by light such as ultraviolet rays emitted from the lamp body 110. For example, the cover 130 may comprise materials, such as fluorinated ethylene propylene (FEP), perfluoroalkoxy (PFA), polytetrafluoroethylene (PTFE), and the like. However, the disclosure is not limited thereto, and the cover 130 may comprise different materials as long as it is capable of scattering light.

The thickness t of the cover 130 may be 0.2 mm or more and 1.5 mm or less. Furthermore, a ratio of the average value r2 of the radius of the outer wall 131 and the radius of the inner wall 132 of the cover 130 to the radius r1 of the lamp body 110 may be 1.5 or more. However, the disclosure is not limited thereto, and the cover 130 and lamp body 110 may have different length dimensions.

The sterilizing apparatus 100 according to an embodiment of the present disclosure may include a fixing member 150 that secures the cover 130 and the lamp body 110.

The fixing members 150 may be provided at opposite ends of the cover 130. As a result, the fixing member 150 may fix the two ends of the cover 130 and the lamp body 110. In this case, the effect of attenuating of an amount of the light emitted from the lamp body 110 may be reduced by the fixing member 150. However, the disclosure is not limited thereto, and the fixing member 150 may have other characteristics as long as the cover 130 is fixed to the lamp body 110. The fixing member 150 may be provided at only one of the two ends of the cover 130.

The fixing member 150 may include a first fixing portion 151 provided on the outer circumferential surface of the lamp body 110, a second fixing portion 152 provided on the cover 130, and at least one connection portion 153 connecting the two fixing portions 151 and 152. The connection portion 153 may include at least one hole 154 to allow the exterior of the cover 130 and the interior of the cover 130 to communicate with each other. In other words, the fixing member 150 may be formed radially. Accordingly, heat generated from the lamp body 100 and the plurality of external electrodes 120 may be easily dissipated to the outside of the sterilizing apparatus 100. However, the disclosure is not limited thereto, and the fixing member 150 may be formed into various shapes, such as a cylindrical shape.

Furthermore, the fixing member 150 may fix the cover 130 and the lamp body 110 such that the inner wall 132 of the cover 130 is arranged to be spaced apart from the outer surface of the plurality of external electrodes 120 in the radial direction of the lamp body 110. Accordingly, heat generated from the lamp body 100 and the plurality of external electrodes 120 may be more easily dissipated to the outside of the sterilizing apparatus 100.

The second fixing portion 152 of the fixing member 150 may be provided on the inner wall 132 of the cover 130. However, the disclosure is not limited thereto, and the second fixing portion 152 may be provided at any position on the cover 130.

The fixing member 150 may comprise a fluororesin-based material to prevent and/or reduce the material from being deteriorated by light such as ultraviolet rays emitted from the lamp body 110. For example, the cover 130 may comprise materials such as FEP, PFA, PTFE, and the like. However, the material of the fixing member 150 is not limited thereto.

The lamp body 110 of the sterilizing apparatus 100 according to an embodiment of the present disclosure may include a gas that emits ultraviolet rays through electric discharge. The plurality of external electrodes 120 to which external power is applied may be provided on the outer circumferential surface of the lamp body 110. As the plurality of cap electrodes 140 are fixed to the opposite ends 111*a* and 111*b* of the lamp body 110, external power may be applied and the applied power may be transmitted to the plurality of external electrodes 120. When power is applied to the plurality of external electrodes 120, ultraviolet rays may be emitted by the gas contained in the lamp body 110. The plurality of external electrodes 120 disposed on the outer circumferential surface of the lamp body 110 may allow the non-light-emitting region 110*b* through which light is not allowed to be transmitted and the light-emitting region 110*a* through which light is allowed to be transmitted to be formed on the outer circumferential surface of the lamp body 110. The light transmitted the light emitting region 110*a* may pass through the cover 130 to be scattered, so that the light may be uniformly irradiated onto an object to be sterilized, such as a cylindrical filter. The cover 130 may be fixed to the lamp body 110 by the fixing member 150.

With such a configuration, the sterilizing apparatus 100 according to an embodiment of the present disclosure may ensure that the cylindrical filter 40 of the air purifier 1 is substantially uniformly irradiated with the light emitted from the lamp body 110, thereby increasing the effect of sterilization of the sterilization device 100.

Figure 10:
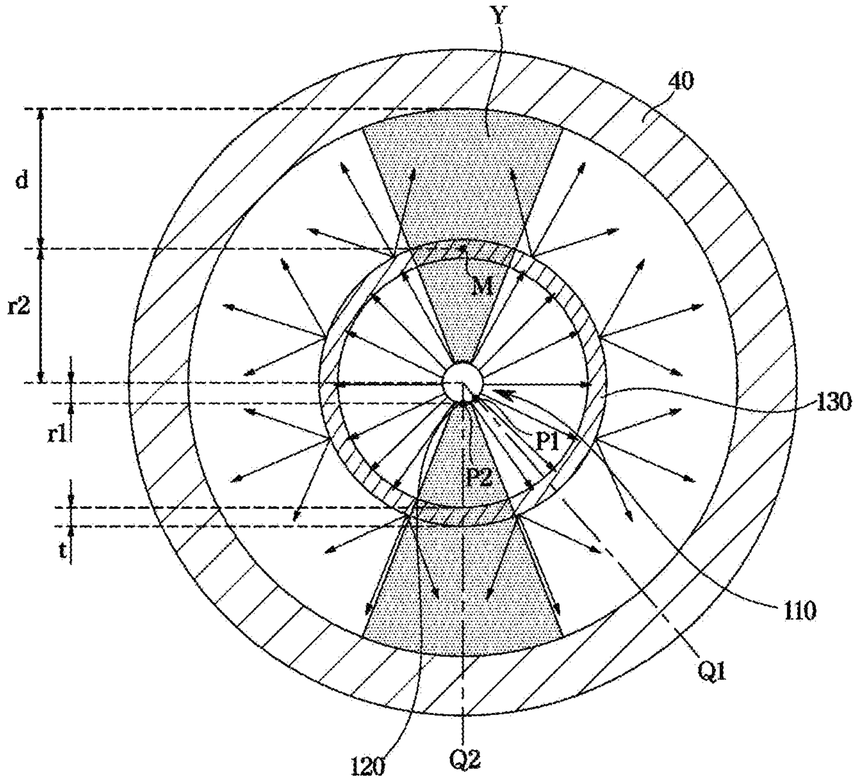
FIG. 10 is a diagram illustrating light emitted from a lamp body of FIG. 3 scattered by a cover according to various embodiments.

FIG. 10 is a cross-sectional view illustrating light emitted from the lamp body according to FIG. 3 being scattered by the cover according to various embodiments.

Referring to FIG. 10, as described above, the filter 40 as shown in FIG. 3 may have the hollow cylindrical shape, and the sterilizing apparatus 100 may be provided within the filter 40. The sterilizing apparatus 100 may include the lamp body 110, the pair of external electrodes 120, and the cover 130. The lamp body 110 may include the light-emitting region 110*a* and the non-light-emitting region 110*b*.

The pair of external electrodes 120 are disposed on the outer circumferential surface of the lamp body 110, and thus the non-light-emitting region 110*b* through which light emitted from the lamp body 110 is not allowed to be transmitted by the pair of external electrodes 120 may be formed. On the outer circumferential surface of the lamp body 110, in response to the non-light-emitting region 110*b*, the light-emitting region 110*a* in which light emitted from the lamp body 110 is allowed to be transmitted may be formed between the pair of external electrodes 120.

Referring to FIG. 10, an external region Y of the non-light-emitting region 110*b* in the radial direction of the lamp body 110 may be defined.

In the conventional sterilizing apparatus (not shown) including the lamp body 110 and the external electrodes 120, the light emitted from the lamp body 110 does not reach the external region Y of the non-light-emitting region 110*b* in the radial direction of the lamp body 110 by the non-light-emitting region 110*b*. As a result, the conventional sterilizing apparatus suffers from the fact that a shaded area (not shown) where ultraviolet rays are not allowed to be irradiated is created on the filter 40, thereby impairing the sterilization function.

In the sterilizing apparatus 100 as shown in FIG. 10, the cover 130 covers at least a portion of the light-emitting region 110*a*, so that the light passing through the light-emitting region 110*a* may pass through the cover 130 to be scattered. Accordingly, the cover 130 may be formed such that at least a portion of the light transmitted through the emitting region 110*a* is scattered in the radial direction of the non-emitting region 110*b* and proceeds along different paths as follows.

A portion of the light scattered while transmitted through the cover 130 may still proceed along a path such that the portion of the light intersects a line Q1 extending in the radial direction of the lamp body 110 so as to pass any point P1 on the light-emitting region 110*a* from the central axis of the lamp body 110. In addition, another portion of the light scattered while transmitted through the cover 130 may proceed along a path such that another portion of the light intersects a line Q2 extending in the radial direction of the lamp body 110 so as to pass any point P2 on the pair of the non-light-emitting region 110*b* from the central axis of the lamp body 110. In other words, the cover 130 may be provided to allow the at least a portion of the light transmitted through the cover 130 to be scattered to the external region Y of the non-light-emitting region 110*b* in the radial direction of the lamp body 110. As a result, the sterilizing apparatus 100 including the cover 130 may allow the light emitted from the lamp body 110 to be uniformly irradiated to the filter 40.

The cover 130 may have the cylindrical shape surrounding the lamp body 110 and the pair of external electrodes 120, and the inner wall 132 of the cover 130 may be arranged to be spaced apart in the radial direction of the lamp body 110 from the outer circumferential surface of the lamp body 110 and the outer surfaces of the pair of external electrodes 120.

In the case of where the cover 130 has the cylindrical shape surrounding the lamp body 110 and the external electrodes 120, the thickness t of the cover 130 may be 0.2 mm or more and 1.5 mm or less. In addition, the ratio of the average value r2 of the radius of the outer wall 131 and the inner wall 132 of the cover 130 to the radius r1 of the lamp body may be formed to be 1.5 or more. However, the specifications of the cover 130 and the lamp body 110 are not limited thereto.

The sterilizing apparatus 100 may be disposed inside the filter 40 such that the cross-section of the filter 40 is concentric with the cross-sections of the lamp body 110 and the cover 130. In this case, the following conditions may be satisfied with respect to the specifications of the cover 130 and the filter 40. The ratio of the average value r2 of the radius of the outer wall 131 and the inner wall 132 of the cover 130 to the distance d from the midpoint M of the outer wall 131 and the inner wall 132 of the cover 130 to the filter 40 may be satisfied to be 2 or less. However, the disclosure is not limited thereto, and the cover 130 and filter 40 may have different specifications in terms of shape and arrangement.

With such a configuration, the sterilizing apparatus 100 according to the embodiment as shown in FIGS. 1 to 10 may ensure that the cylindrical filter 40 of the air purifier 1 is uniformly irradiated with the light emitted from the lamp body 110, thereby increasing the effect of sterilization of the sterilization device 100.

Furthermore, in FIGS. 1 to 10, the sterilizing apparatus 100 has been described as being included in the air purifier 1 to sterilize the cylindrical filter 40 of the air purifier 1, but is not limited thereto. The sterilizing apparatus 100 may be included in other home appliances, such as vacuum cleaners, air conditioners, and dehumidifiers, and may sterilize non-cylindrical filters or other non-filter components.

Figure 11:
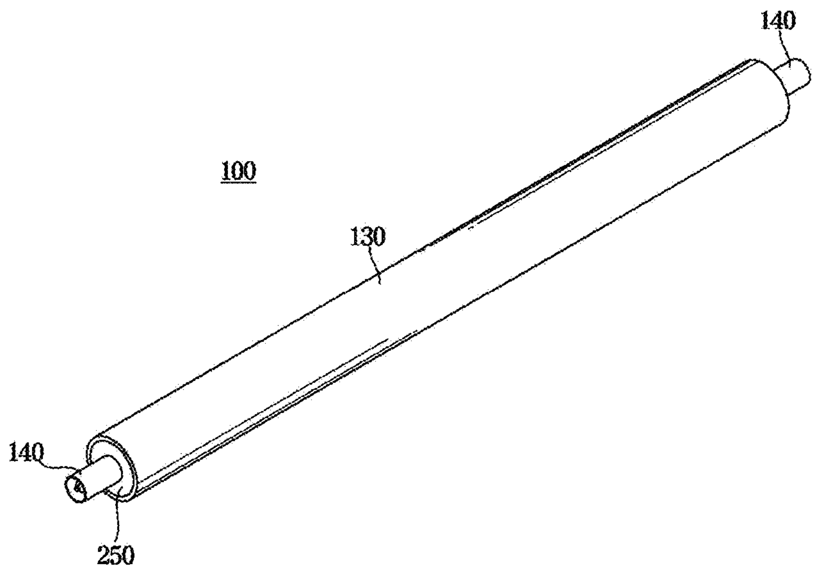
FIG. 11 is a perspective view illustrating a sterilizing apparatus according to various embodiments.
Figure 12:
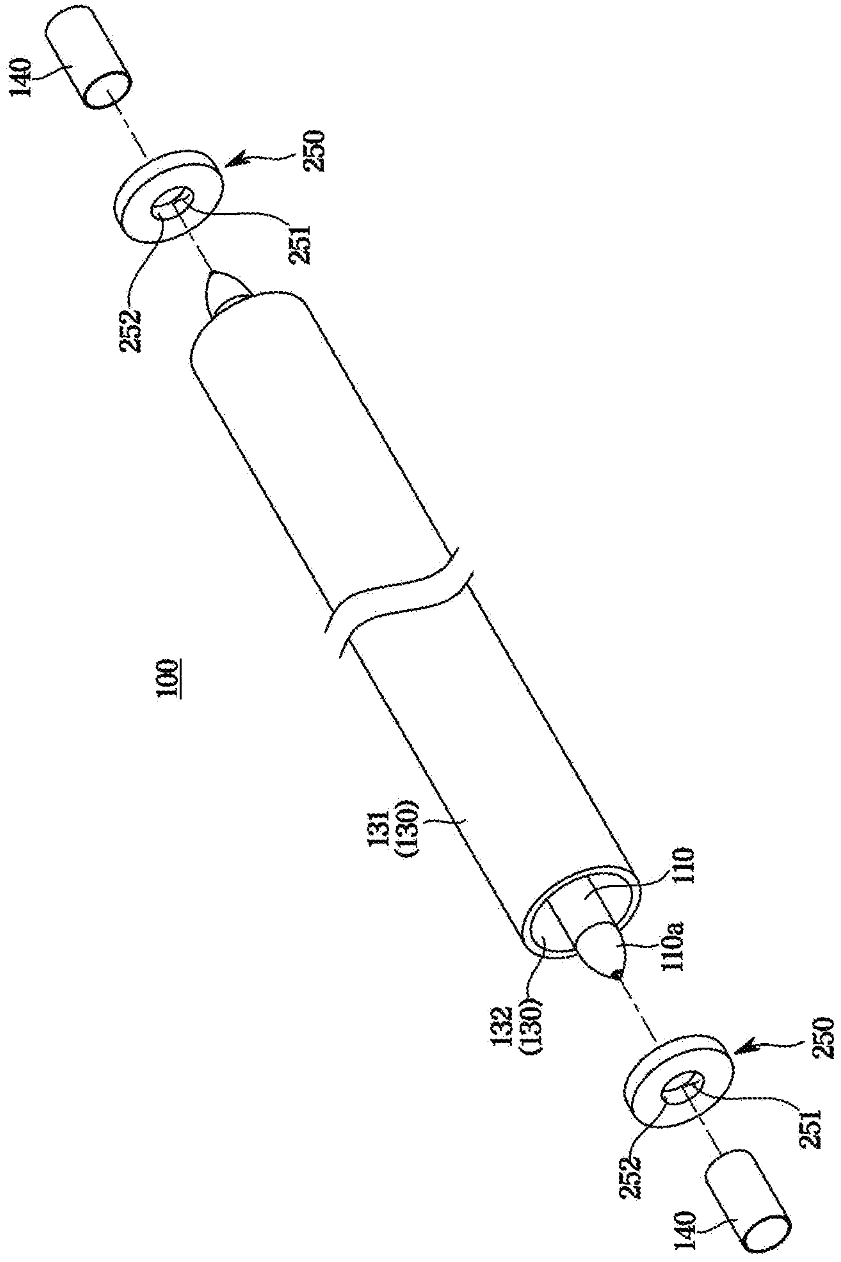
FIG. 12 is an exploded perspective view illustrating a disassembled fixing member in the sterilizing apparatus of FIG. 11 according to various embodiments.

FIG. 11 is a perspective view illustrating a sterilizing apparatus according to various embodiments. FIG. 12 is an exploded perspective view illustrating the disassembled fixing member in the sterilizing apparatus of FIG. 11 according to various embodiments.

Referring to FIGS. 11 and 12, a sterilizing apparatus and a home appliance including the same according to an embodiment of the present disclosure is described below. In describing the embodiment shown in FIGS. 11 and 12, the same reference numerals may be assigned to the same components as those shown in FIGS. 1 to 10 and the description thereof may be omitted.

According to an embodiment, for ease of description, an air purifier, which is a type of home appliance, is described as an example. However, the configuration including a sterilizing apparatus according to an embodiment of the present disclosure is not limited to air purifiers, and may be used with respect to any home appliance requiring sterilization using light.

The air purifier 1 may include the housing 10, the inlet 20 and the outlet 30 provided in the housing 10, the filter 40, the blowing fan 50, and the sterilizing apparatus 100. The sterilizing apparatus 100 may be coupled to the filter 40 by the supporter 60. However, the disclosure is not limited thereto, and the sterilizing apparatus 100 may not be coupled to the filter 40.

The filter 40 may have a hollow cylindrical shape. The sterilizing apparatus 100 may be provided within the filter 40 in a direction parallel to the filter 40. However, the disclosure is not limited thereto, and the shape of the filter 40 may be a rectangular parallelepiped with a hollow shape, etc.

The sterilizing apparatus 100 may include the lamp body 110, the external electrodes 120, and the cover 130. The lamp body 110 may contain a gas that emits ultraviolet rays through electric discharge and may have a cylindrical shape. The external electrode 120 may each be disposed on the outer circumferential surface of the lamp body 110 and extend in the longitudinal direction of the lamp body 110. The external electrodes 120 may be provided in a plurality, and may be provided in pairs.

The cover 130 may include the inner wall 132 and the outer wall 131 and may be provided in the radial direction of the lamp body 110. The inner wall 132 of the cover 130 may face the outer circumferential surface of the lamp body 110 and the outer surfaces of the plurality of external electrodes 120.

The light-emitting region 110*a*, which is provided between the plurality of external electrodes 120 and through which light emitted from the lamp body 110 is allowed to be transmitted, may be formed on the outer circumferential surface of the lamp body 110. In response to the light-emitting region 110*a*, the non-light-emitting region 110*b* through which light emitted from the lamp body 110 is not allowed to be transmitted due to the plurality of external electrodes 120, may be formed on the outer circumferential surface of the lamp body 110.

The cover 130 may be provided to cover at least a portion of the light-emitting region 110*a* and scatter the light emitted from the lamp body 110. As a result, the light emitted from the lamp body 110 may be uniformly irradiated to the filter 40.

Referring to FIGS. 11 and 12, the sterilizing apparatus 100 according to the present embodiment may include a fixing member 250 for securing the cover 130 and the lamp body 110.

The fixing members 250 may be provided at opposite ends of the cover 130 to fix the two ends of the lamp body 110 and the cover 130. As a result, the fixing member 250 may fix the opposite ends of the cover 130 and the lamp body 110. In this case, the effect of attenuating of the amount of light emitted from the lamp body 110 by the fixing member 250 may be reduced. However, the disclosure is not limited thereto, and the fixing member 250 may have other characteristics as long as the cover 130 is fixed to the lamp body 110. The fixing member 250 may be provided at only one of the opposite ends of the cover 130.

The fixing member 250 may be formed in a cylindrical shape including a hollow 251 and an inner surface 252 forming the hollow 251. In addition, the inner surface 252 of the fixing member 250 may be connected to the lamp body 110 and may be connected to the inner wall 132 of the cover 130. However, the disclosure is not limited thereto, and the fixing member 250 may be formed in different shapes.

The fixing member 250 may fix the cover 130 and the lamp body 110 such that the inner wall 132 of the cover 130 is arranged to be spaced apart from the outer surface of the plurality of external electrodes 120 in the radial direction of the lamp body 110. However, the disclosure is not limited thereto, and the fixing member 250 may be formed such that the inner wall 132 of the cover 130 is in close contact with the inner wall of the external electrode 120.

With such a configuration, the sterilizing apparatus 100 according to an embodiment of the present disclosure may allow the light emitted from the lamp body 110 to be uniformly irradiated to the cylindrical filter 40 of the air purifier 1.

In the above description, the radius r1 of the lamp body 110, the average value r2 of the radius of the outer wall 131 and the inner wall 132 of the cover 130, and the distance d from the midpoint M of the outer wall 131 and the inner wall 132 of the cover 130 to the filter 40 may each be treated as independent variables.

While the present disclosure has been illustrated and described with reference to various example embodiments, it will be understood that the various example embodiments are intended to be illustrative, not limiting. It will be further understood by those skilled in the art that various changes in form and detail may be made without departing from the spirit and scope of the present disclosure, including the appended claims and their equivalents. It will also be understood that any of the embodiment(s) described herein may be used in conjunction with any other embodiment(s) described herein.

What is claimed is:

1. A sterilizing apparatus, comprising:

a lamp body containing a gas configured to emit ultraviolet rays through electric discharge, and having a cylindrical shape;

a plurality of external electrodes disposed on an outer circumferential surface of the lamp body and extending in a longitudinal direction of the lamp body; and a cover including an inner wall and an outer wall, and provided in a radial direction of the lamp body wherein the inner wall faces the outer circumferential surface of the lamp body and outer surfaces of the plurality of external electrodes;

wherein the lamp body includes a light-emitting region provided on the outer circumferential surface of the lamp body, the light-emitting region disposed between the plurality of external electrodes to allow light emitted from the lamp body to be transmitted, and the cover is configured to cover at least a portion of the light-emitting region and is configured to scatter the light emitted from the lamp body.

2. The sterilizing apparatus of claim 1, wherein the inner wall of the cover is spaced apart in the radial direction of the lamp body from the outer circumferential surface of the lamp body and the outer surfaces of the plurality of external electrodes.

3. The sterilizing apparatus of claim 1, wherein the cover has a cylindrical shape surrounding the lamp body and the plurality of external electrodes.

4. The sterilizing apparatus of claim 3, wherein a cross-section of the cover is concentric with a cross-section of the lamp body.

5. The sterilizing apparatus of claim 4, wherein based on an average value of the radius of the outer wall and the inner wall of the cover being r2 and the radius of the lamp body being r1, a ratio of r2 and r1 is 1.5 or more.

6. The sterilizing apparatus of claim 3, wherein the cover has a thickness of 0.2 mm or more and 1.5 mm or less.

7. The sterilizing apparatus of claim 1, wherein the lamp body includes a non-light-emitting region on the outer circumferential surface of the lamp body, the non-light-emitting region wherein light emitted from the lamp body is blocked by the plurality of external electrodes, and the cover is configured to scatter at least a portion of the light transmitted through the cover in a direction corresponding to a radial direction of the non-light-emitting region.

8. The sterilizing apparatus of claim 1, further comprising a fixing piece configured to fix the cover and the lamp body.

9. The sterilizing apparatus of claim 8, wherein the fixing piece is provided at opposites ends of the cover and configured to fix the lamp body and the opposite ends of the cover.

10. The sterilizing apparatus of claim 8, wherein the fixing piece includes a first fixing portion provided on the outer circumferential surface of the lamp body, a second fixing portion provided on the cover, and at least one connection portion connecting the first fixing portion and the second fixing portion, and the connection portion includes at least one hole configured to allow the exterior of the cover to communicate with the interior of the cover.

11. The sterilizing apparatus of claim 8, wherein the fixing piece has a cylindrical shape including a hollow and an inner surface forming the hollow, wherein the inner surface is connected to the lamp body.

12. The sterilizing apparatus of claim 8, wherein the cover and the lamp body are fixed by the fixing piece so that the inner wall of the cover is spaced apart from the outer surfaces of the plurality of external electrodes in the radial direction of the lamp body.

13. The sterilizing apparatus of claim 1, further comprising a plurality of cap electrodes fixed to opposite ends of the lamp body and configured to apply power to the plurality of external electrodes, wherein each of the plurality of external electrodes is connected to only one of the plurality of cap electrodes.

14. The sterilizing apparatus of claim 13, wherein the plurality of cap electrodes have a cylindrical shape including a hollow.

15. The sterilizing apparatus of claim 1, wherein the cover comprises a fluororesin material.

16. A home appliance, comprising:

an inlet configured to draw in air;

a blowing fan;

a filter having a cylindrical shape including a hollow and configured to purify the air entering the inlet;

an outlet configured to discharge air passing through the filter;

a sterilizing apparatus comprising a lamp disposed inside the filter; and a housing including the inlet and the outlet and including the blowing fan, the filter and the sterilizing apparatus, wherein the sterilizing apparatus includes:

a lamp body containing a gas configured to emit ultraviolet rays through electric discharge and having a cylindrical shape;

a pair of external electrodes extending in a longitudinal direction of the lamp body and disposed on an outer circumferential surface of the lamp body to face each other with respect to a central axis of the lamp body; and a cover including an inner wall and an outer wall provided in a radial direction of the lamp body to allow the inner wall to face the outer circumferential surface of the lamp body and outer surfaces of the pair of external electrodes, wherein the lamp body includes a light-emitting region on the outer circumferential surface of the lamp body, the light-emitting region disposed between the pair of external electrodes configured to allow light emitted from the lamp body to be transmitted, wherein the cover is configured to cover at least a portion of the light-emitting region and to scatter the light emitted from the lamp body.

17. The sterilizing apparatus of claim 16, wherein the sterilizing apparatus may further comprise a support configured to be coupled to the filter.

18. The sterilizing apparatus of claim 17, wherein the support may be formed radially.

19. The sterilizing apparatus of claim 16, wherein cross-sections of the cover and the lamp body may be arranged to be concentric with a cross-section of the filter, and wherein based on an average value of a radius of the outer wall and the inner wall of the cover being r2 and a radius of the lamp body being r1, a ratio of r2 and r1 may be 2 or less.

* * * * *